(12) United States Patent
Miller et al.

(10) Patent No.: US 11,547,408 B2
(45) Date of Patent: *Jan. 10, 2023

(54) METHOD AND APPARATUS FOR DELIVERING MULTIPLE TISSUE FASTENERS

(71) Applicant: Amsel Medical Corporation, Cambridge, MA (US)

(72) Inventors: Arnold Miller, Cambridge, MA (US); Raanan Miller, Cambridge, MA (US); Nir Lilach, Kfar Yehoshua (IL); William Edelman, Sharon, MA (US)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 664 days.

This patent is subject to a terminal disclaimer.

(21) Appl. No.: 15/699,577

(22) Filed: Sep. 8, 2017

(65) Prior Publication Data

US 2021/0196273 A1  Jul. 1, 2021

Related U.S. Application Data

(63) Continuation-in-part of application No. 15/226,577, filed on Aug. 2, 2016, now abandoned.

(60) Provisional application No. 62/298,724, filed on Feb. 23, 2016.

(51) Int. Cl.
| | | |
|---|---|---|
| *A61B 17/128* | (2006.01) | |
| *A61B 17/08* | (2006.01) | |
| *A61B 17/122* | (2006.01) | |
| *A61B 17/12* | (2006.01) | |
| *A61B 17/10* | (2006.01) | |

(52) U.S. Cl.
CPC .............. *A61B 17/08* (2013.01); *A61B 17/10* (2013.01); *A61B 17/12* (2013.01); *A61B 17/122* (2013.01); *A61B 17/128* (2013.01); *A61B 2017/081* (2013.01)

(58) Field of Classification Search
CPC ....... A61B 17/10; A61B 17/12; A61B 17/128; A61B 17/1285; A61B 2017/12004
See application file for complete search history.

(56) References Cited

U.S. PATENT DOCUMENTS 9,936,955 B2 * 4/2018 Miller ................ A61B 17/1214

\* cited by examiner

*Primary Examiner* — Melanie R Tyson

(57) ABSTRACT

Method and apparatus for delivering multiple tissue fasteners with needle and fastener assemblies each of which comprises a hollow needle adapted to be passed through tissue layers to be fastened, the needle containing a proximal and a distal implant, the implants being configured to self-expand when ejected from the needle, the implants being lockable to each other after ejection in response to drawing the implants together with tissue gripped between the implants.

23 Claims, 13 Drawing Sheets

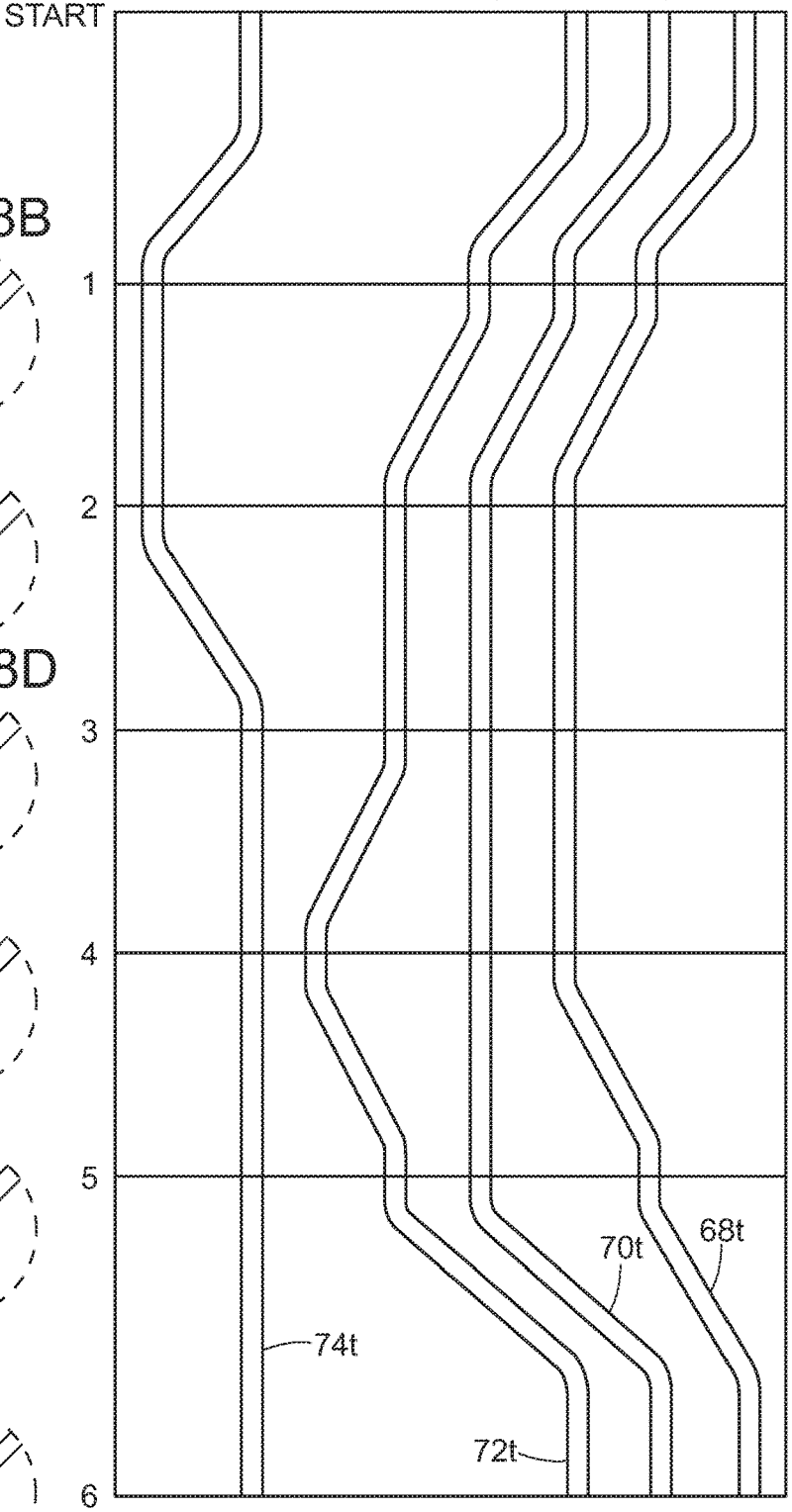
FIG. 18
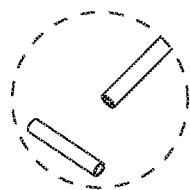
FIG. 18A
FIG. 18B
FIG. 18C
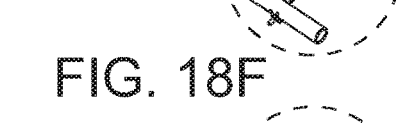
FIG. 18D
FIG. 18E
FIG. 18F
FIG. 18G
FIG. 18H
FIG. 18I
FIG. 18J

METHOD AND APPARATUS FOR DELIVERING MULTIPLE TISSUE FASTENERS

RELATED APPLICATIONS

This application is a continuation-in-part of U.S. patent application Ser. No. 14/639,814, filed Mar. 5, 2015 and Ser. No. 14/272,304 filed May 7, 2014 and is related to other applications identified in the Application Data Sheet submitted with this application.

FIELD

Devices and methods for delivery of multiple tissue fasteners to occlude body lumens and/or to secure tissue layers together.

BACKGROUND

U.S. patent applications Ser. No. 15/438,924, filed, Feb. 22, 2017 and Ser. No. 14/272,304 filed May 7, 20214 describe tissue fasteners comprising a pair of implants (sometimes referred to as "occluders") that can be positioned on opposite sides of two or more layers of tissue to transfix the layers and clamp and secure the layers together while effecting a seal that circumscribes the point of transfixion. The tissue layers may be opposing walls of a body lumen or hollow anatomical structure, for example, if it is desired to occlude the lumen or structure, or may be simply tissues that are to be attached to each other as desired by a clinician in the performance of a particular surgical procedure. It would be desirable to be able to deploy a number of such implants in rapid succession without having to remove or reload the delivery and deployment device, for example, in laparoscopic procedures, in which numerous insertions and retractions of devices from within the patient are to be avoided.

SUMMARY

The invention provides a delivery device that is preloaded with a plurality of fastener assemblies and accompanying control mechanisms associated with each fastener assembly by which one of the fastener assemblies can be selected for deployment and in which the device sequentially operates the control mechanisms associated with the selected fastener assembly to deploy that fastener assembly to attach it to tissue. Upon deployment of a selected fastener the device is indexed to position another of the fastener assemblies and its control mechanisms in readiness for deployment.

THE DRAWINGS

The various objects and advantages of the invention will be appreciated more fully from the following description, with reference to the accompanying drawings in which:

FIG. 18 is a plan illustration of the cam tracks and the configuration of the FIGS. 18A-18J are illustrations of the corresponding configurations of the distal end of the device as it interacts with tissue at the stages of operation of the device.

DETAILED DESCRIPTION

In the following description and claims terms such as upper, lower, forward, rearward, distal and proximal are used in a relative sense and for convenience to illustrate relative positions or orientations of components of the invention as well as relative directions.

Figure 1:
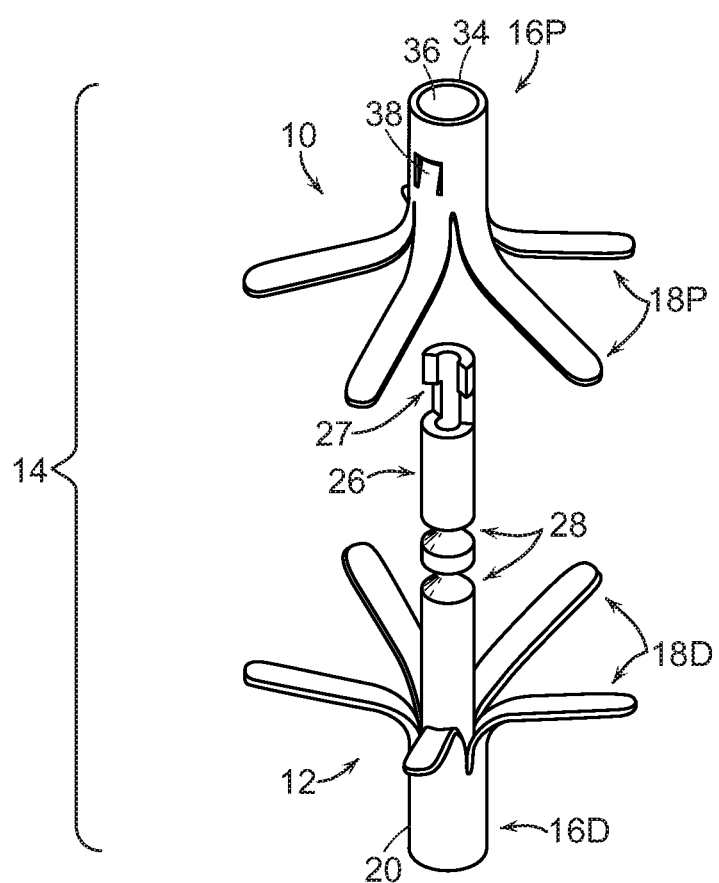
FIG. 1 is an illustration of the components of a fastener assembly as may be used in the practiced of the invention.

Exemplary fasteners are illustrated in FIG. 1 and include a proximal implant 10 and a distal implant 12 (sometimes referred to as "occluders") that, together, cooperate to form a fastener assembly, indicated generally at 14. Although the implants may take different forms, each is characterized by having a body, indicated generally at 16P, 16D and a plurality of legs, indicated generally at 18P, 18D, that extend radially from the body 16 (the letters "P" and "D" indicating like or similar elements of the proximal or distal implants, respectively). The implants may be formed from an elastic material, such as a superelastic Nitinol alloy, and may be configured so that in an unstressed, relaxed state the legs 18P, 18D extend radially from their respective bodies 16P, 16D. The legs 18P, 18D can be elastically deformed to extend in an axial direction so that the implants 10, 12 can be contained in a delivery tube such as a hollow needle. When an implant is ejected from the delivery tube its legs self-expand to their relaxed shape in which the legs 18 extend radially outward from the body 16. Preferably, the legs of each implant define a conical or concave configuration when relaxed. The tubular body of one of the implants (usually the proximal implant 10) in a fastener assembly may be arranged to receive, telescopically, a portion of the body of the other implant (usually the distal implant) or a proximal extension of that body. The implants 10, 12 include a latching mechanism by which, when the proximal and distal implants of a fastener assembly are brought together, cause the implants to lock together. Tissue layers disposed between the legs of the implants are securely clamped together with connected portions of the fastener assembly transfixing the tissue layers.

In one embodiment, distal implant 12 comprises a tubular body 16D having a distal end 20 and a lumen. A proximally extending locking tube or rod 26 is located within and secured within the lumen of the body 16D. In this embodiment locking tube 26 of the distal implant is provided with one or more longitudinally spaced circumferential grooves or recesses 28 formed along its length. The locking tube is provided, at its proximal end, with a portion 27 of a mechanical interlock that detachably couples with a cooperative interlock portion 29 at the distal end of a distal implant retention shaft 31 that facilitates delivery of the fastener assembly, as described below. A tubular portion of the body 16D is slit along a portion of its length to define a plurality of legs 18D that, when the body is in an unstressed configuration, extend radially outward as shown in FIG. 1 and, preferably, define a somewhat concave or conical configuration. Here, again, legs 18D can be deformed resiliently to a tubular, substantially linear, low profile shape so that they can be constrained within the lumen of a delivery tube or needle and, when the constraint is removed, the elasticity of the material of the body 16D causes legs 18D to return to their relaxed, expanded position shown in FIG. 1.

As shown in FIG. 1 the proximal implant 10 may comprise a tubular body 16P having a distal end, a proximal end 34, and a lumen 36 adapted to receive, telescopically, the locking rod 26 of the distal implant 12. Tubular body 16P is slit at its distal end to define a plurality of legs 18P. One or more inwardly projecting tangs 38 are formed in tubular body 16P adjacent its proximal end 34. Proximal implant 10 preferably is formed out of the same or similar material as the distal implant and is constructed so that its legs 18P normally project laterally away from the longitudinal axis of tubular body 30 (e.g., in the manner shown in FIG. 1). Legs 18P can be constrained inwardly to a low-profile configuration so that proximal implant 10 can assume a substantially linear disposition to be contained within the lumen of the delivery needle but will return to their radially expanded position shown in FIG. 1 when ejected from the needle. Preferably, the implants are configured so that when they are brought together and locked to each other, the legs of the proximal implant will interdigitate with the legs of the distal implant. The distal and proximal implants 12, 10 can be mated with locking tube 26 of distal implant body 16D being received in the lumen 36 of proximal implant 10. The proximity of the locked implants to each other and the degree of interdigitation of the legs may depend, in part, on which groove 28 of the locking rod 26 is engaged by a tang 38 on the proximal implant.

Figure 12:
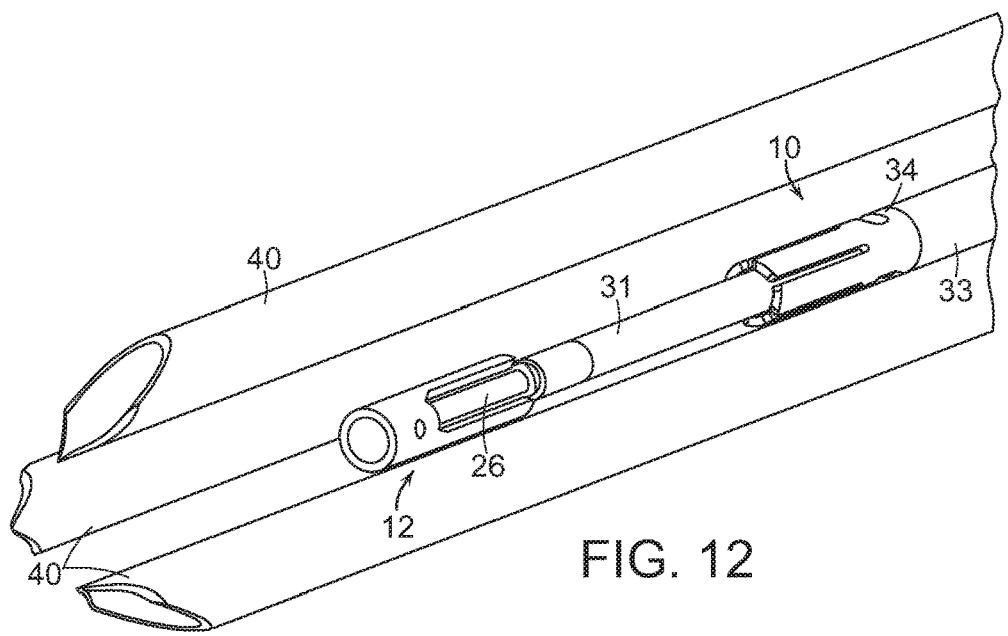
FIG. 12 is an enlarged, partly broken away, illustration of the proximal and distal implants as they are constrained in a needle in readiness to be advanced out of a needle.

When assembled and in readiness for delivery, the proximal and distal implants 10, 12 are contained in tandem within the lumen of a delivery needle 40 with their legs 18P, 18D constrained in a low, generally tubular, profile (FIG. 12). The distal end of a distal implant retention shaft 31 is interlocked with the proximal interlock element 29 at the end of the locking shaft 26 and the proximal implant 10 is disposed about the distal implant retention shaft 31 and within an annular space that exists between the retention shaft 31 and needle 40. The connection at the mechanical interlock may be secured by a removable or retractable rod (not shown) that extends through the retention shaft 31 and locking tube 26 or, alternately, by a removable retractable overtube (not shown) that extends over the interlock. Additionally, the assembly includes a proximal implant pusher tube 33 disposed in the space between the retention shaft 31 and the needle 40 and abuts the proximal end 34 of the proximal implant 10.

Figure 2:
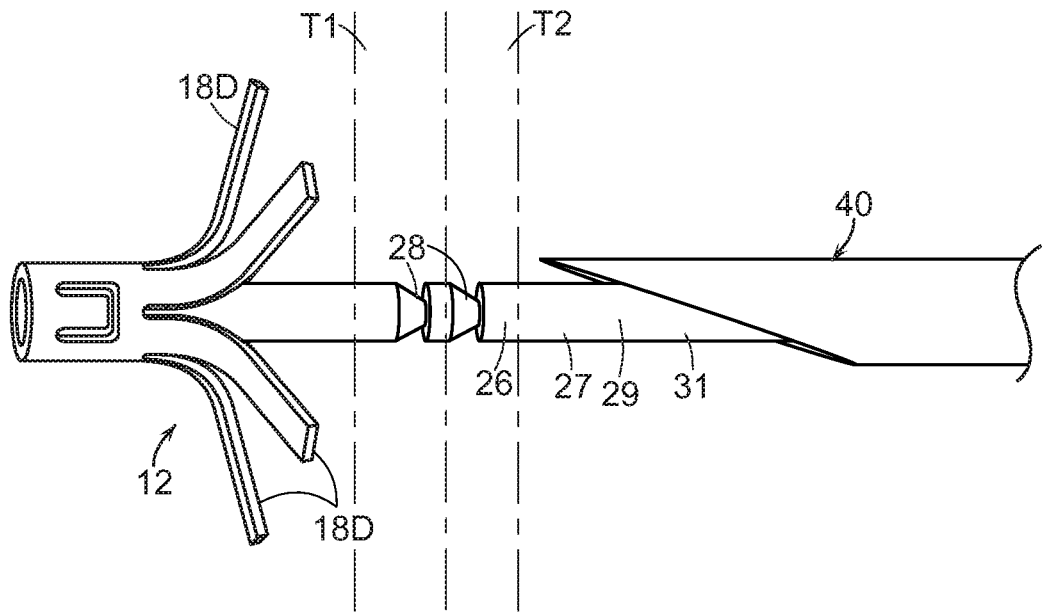
FIG. 2 is an enlarged illustration of the distal implant of the fastener assembly after the needle has been passed through the tissue layers and the distal implant has advanced out of the needle and with it legs self-deployed.

The manner in which a fastener assembly 14 may be deployed is illustrated in FIGS. 2-6. A hollow needle 40 containing both the distal and proximal devices (FIG. 12), arranged in tandem within the needle lumen, is advanced to the deployment site. If the needle is housed in a protective sheath of a delivery device, the sheath is retracted or the needle is extended to expose the distal end of the needle. The needle may have a sharp, tissue piercing tip or may be blunt if the tissue has already been pierced. The needle then is passed transversely through the tissue layers (e.g., the walls of the blood vessel to be occluded) or objects to be secured to one another, illustrated diagrammatically in phantom as T1 and T2. At this point in the procedure, the implants are constrained in a low-profile configuration within the needle and, depending on the spacing of the tandem implants within the needle, may be on opposite sides of the vessel or tissue layers to be clamped. With the distal end of the hollow needle 40 placed distally beyond the tissue, the needle is retracted proximally to progressively expose the distal implant 12 and to allow legs 18D of distal implant 12 to expand radially on the far side of the blood vessel or tissue (FIG. 2). The distal implant is retained in place by its mechanical interlock 27,29 with the retention tube 31. At this point, distal implant locking tube 26 extends proximally through and transfixes the blood vessel or tissue layers, assuring that the device cannot be dislodged.

Figure 3:
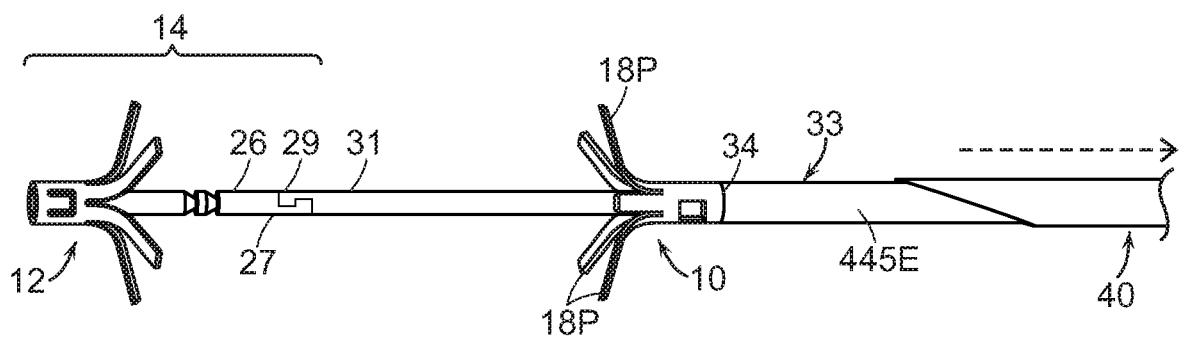
FIG. 3 is an illustration of the device after the proximal implant has advanced out of the needle with its legs self-deployed.

Then, with retention tube 31 and distal implant 12 engage and held in place, needle 40 is withdrawn further proximally until proximal implant 10 is exposed and is no longer constrained within hollow needle 40 (FIG. 3). As this occurs, legs 18P of proximal implant 10 are released fully from the constraint of hollow needle 40 and self-expand to their deployed configuration on the near side of the tissue.

Figure 4:
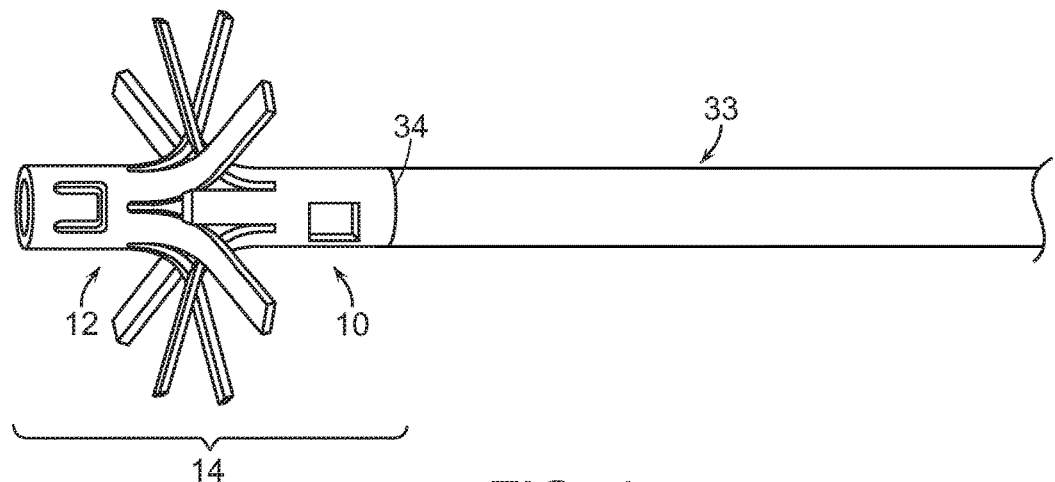
FIG. 4 is an illustration of the proximal and distal implants of the fastener assembly drawn together in the absence of tissue and showing the manner in which the legs of the implants are interdigitated.
Figure 5:
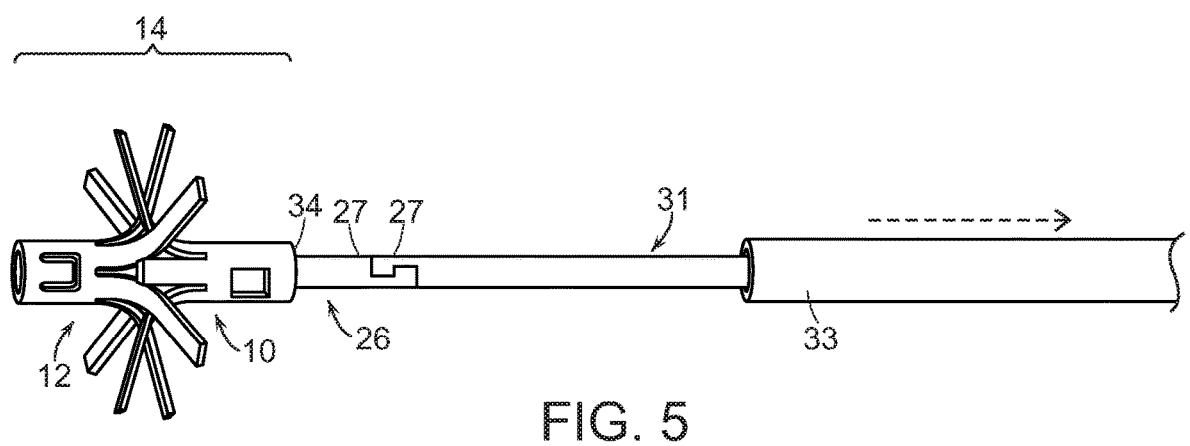
FIG. 5 is an illustration similar to FIG. 4 in which the proximal implant pusher tube has been retracted.
Figure 6:
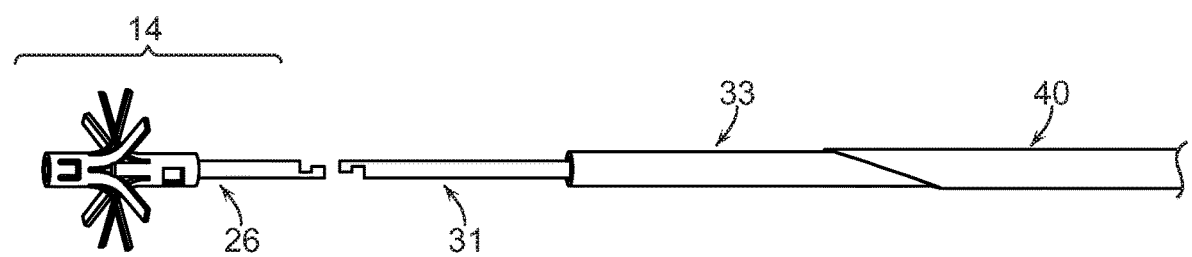
FIG. 6 is an illustration of the deployment device after it has been separated from the tissue fastener.

Proximal implant pusher tube 33 then is advanced distally along and about the retention tube 31 to push the proximal implant 10 toward distal implant 12 (FIG. 4). As distal implant 12 and proximal implant 10 are drawn together, their legs 18D, 18P compress the blood vessel walls or tissue layers therebetween, thereby transfixing and occluding the blood vessel or clamping the tissue. Distal implant 12 and proximal implant 10 continue moving together until inwardly-projecting tangs 38 of proximal implant 10 enter a selected circumferential groove or recess 28 of distal implant 12, thereby locking the two members into position relative to one another. Proximal implant pusher tube 33 is withdrawn (FIG. 5), the locking pin 25 or overtube is withdrawn, retention tube 31 is released from distal implant 12 to unlock the second half 29 of the mechanical interlock from the first half 27 of the mechanical interlock, and then the installation device is withdrawn (FIG. 6).

Figure 7:
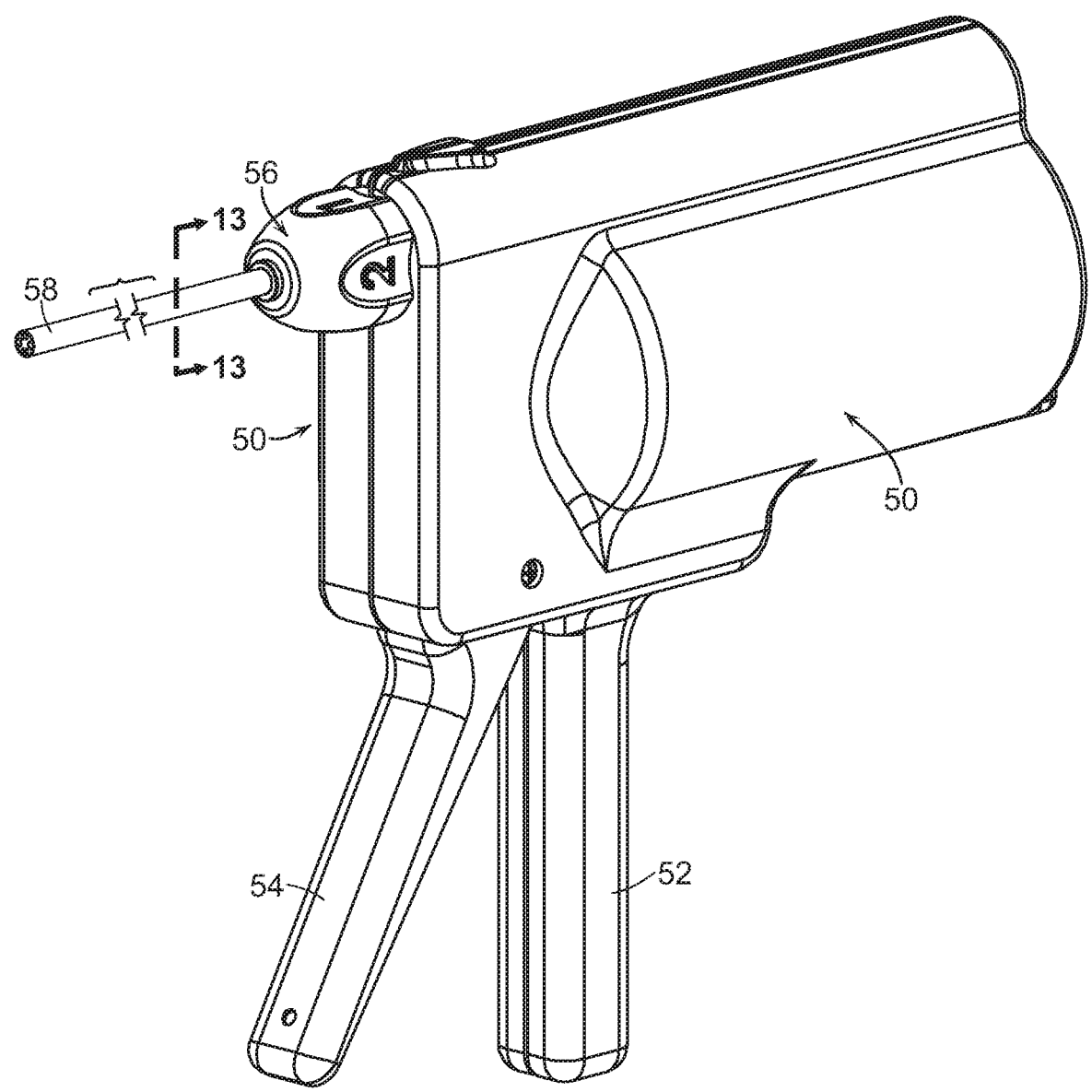
FIG. 7 is an illustration of the device for deploying a plurality of tissue fasteners.
Figure 8:
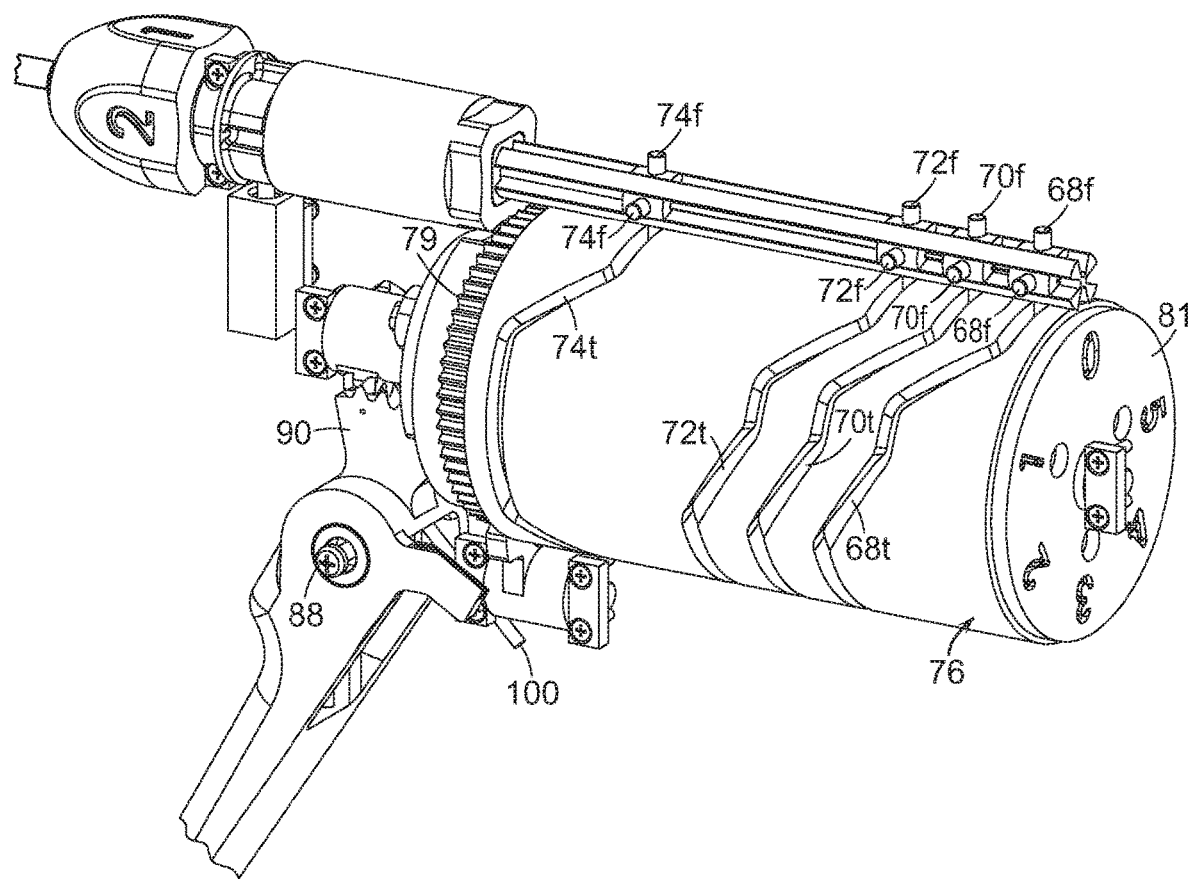
FIG. 8 is an illustration of the device with the housing removed and showing the internal operating elements of the device.
Figure 9:
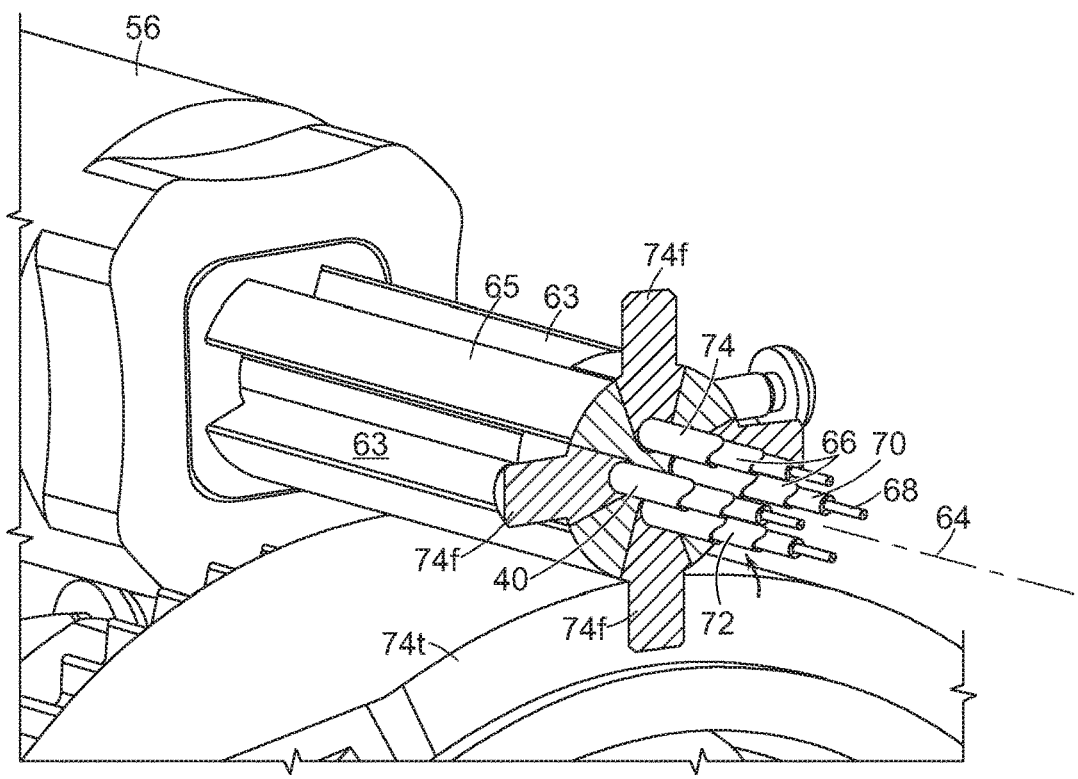
FIG. 9 is an illustration, partly broken away and partly in section, of a portion of the hub, the control rod support with channels for control rod groups and four sets of control rods.
Figure 10:
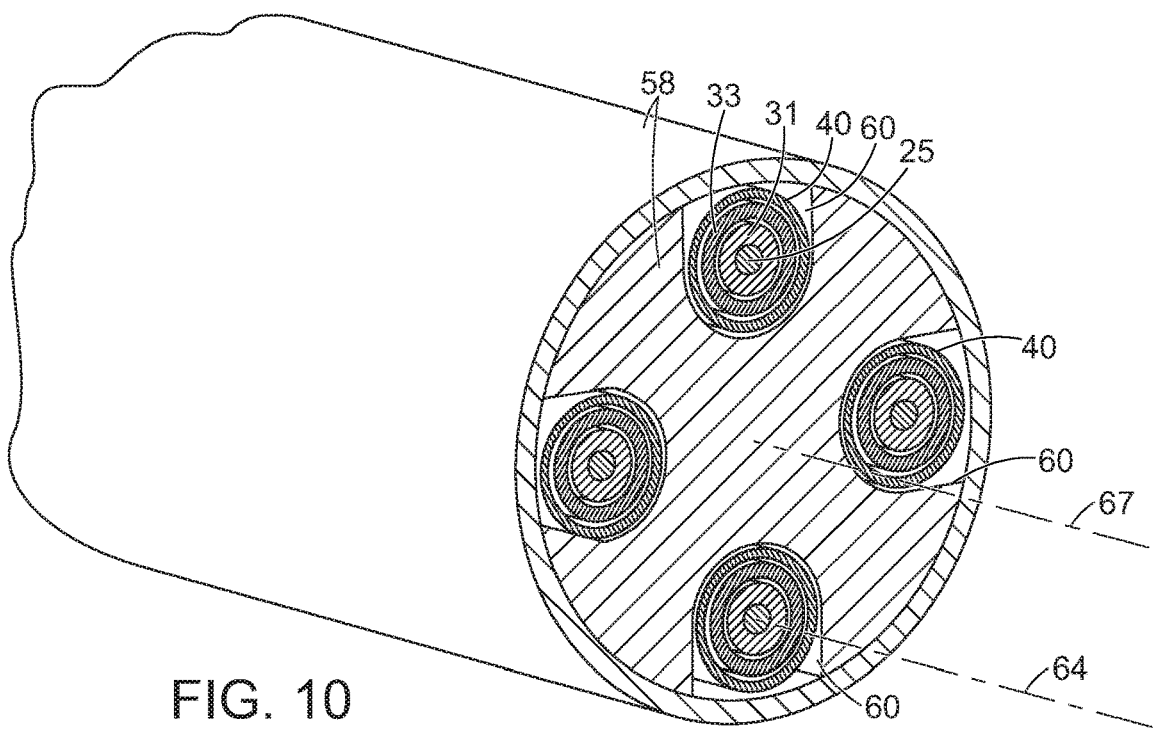
FIG. 10 is an enlarged isometric cross section of the wand containing four needle and fastener assemblies and associated control members.

For many surgical procedures, for example, in laparoscopic surgery, it would be desirable to be able to install a plurality of such tissue fasteners in quick succession without having to withdraw the delivery device from the surgical field to reload it or to replace it with another. To that end, the invention provides a device for delivering multiple fasteners to the surgical site. FIG. 7 shows an illustrative embodiment of a device for delivering multiple fasteners in quick succession without removing the delivery device from the surgical field. The device includes a frame 50 that may be in the form of a housing and may include a pistol-grip handle 52 and a trigger 54 that drives a mechanism for delivering the fasteners. A hub 56 is rotatably mounted to the forward end of the frame 50 for rotation about a central axis 67 and a forwardly extending wand 58 is attached to and extends distally from the hub 56 for rotation with the hub (FIG. 10). Each of the hub 56 and the wand 58 has a plurality of longitudinally extending channels 60 each of which contains a needle 40 pre-loaded with tandem proximal and distal implants 10, 12 and associated components to deliver and deploy the implants (FIG. 9). The hub 56 may be rotated manually about the central axis 67 to align a selected one of the channels 60 and its needle and fastener assembly 62 with a slightly offset paralleling axis 64 of the device (FIG. 10). The offset axis 64 may be considered as the "active" or "delivery" axis.

Figure 13:
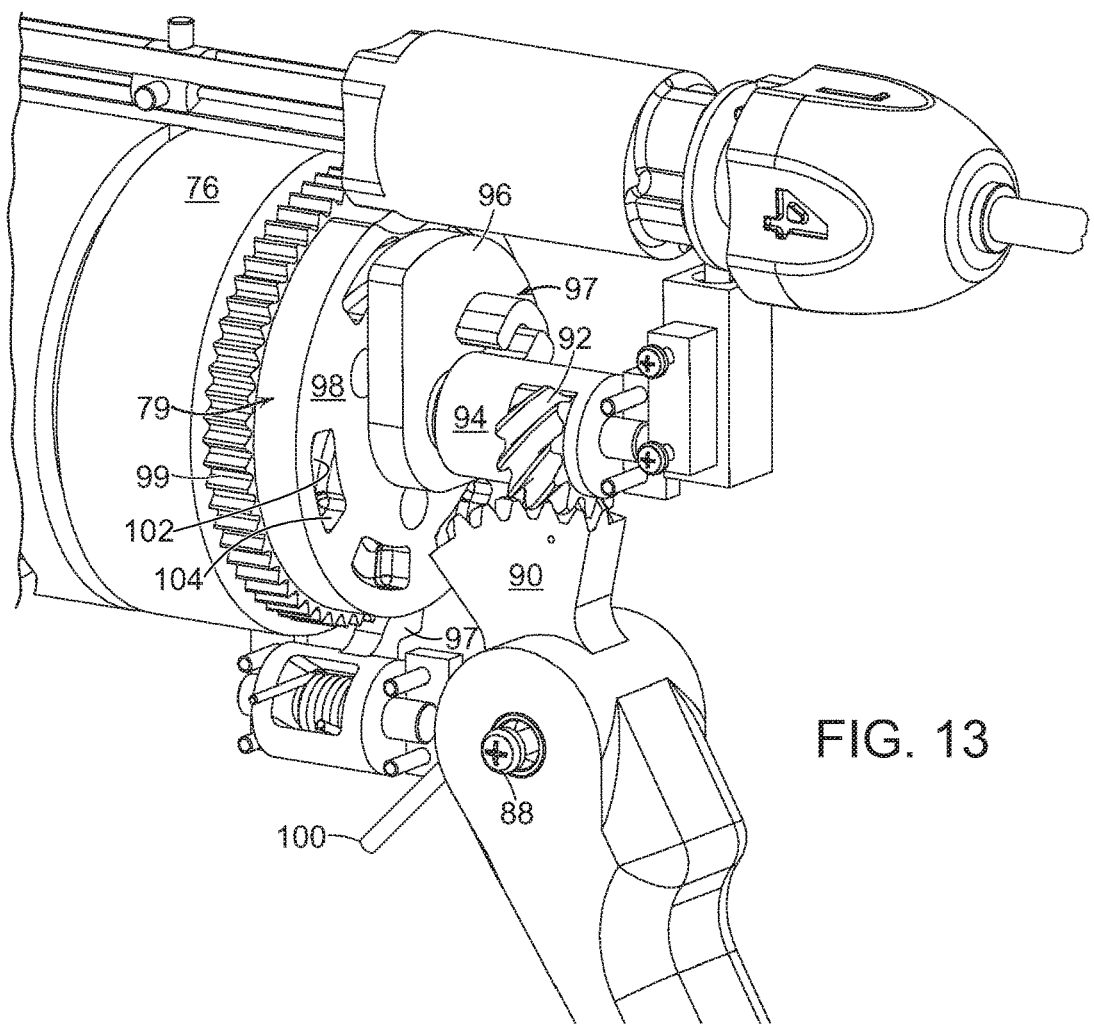
FIG. 13 is an isometric illustration of the front end of the drive mechanism from an angle different from FIG. 11.

Each needle and fastener assembly 62 includes a group 66 of proximally extending control members such as control rods (FIG. 9) that are connected to the components of the needle and fastener assembly 62 to control forward and rearward movement of the needle 40, the retention shaft 31, the proximal pusher tube 33 and the retractable locking rod 25. Each group 66 of control rods is supported within a rearwardly extending channel 63 formed in a rearwardly extending control rod support 65 that is attached to and is rotatable with the hub 56. Although, in the illustrative embodiment, four needle and fastener assembly groups 66 are shown, each of which is contained and supported by one of four channels 63 of the control rod support 65, it should be understood that the invention may be practiced with other numbers of needle and fastener assembly groups 66. The control rods in each group 66 may be tubular and may be arranged concentrically with the innermost control rod 68 being connected to the removable lock rod 25, the next surrounding control rod 70 being connected to the proximal implant push tube 33, the next surrounding control rod 72 being connected to the retention shaft 31 and the outermost control rod 74 being connected to the needle 40 (FIG. 13). The control rods 68, 70, 72 and 74 may be formed as integral extensions of their associated components.

The movement of the control rods and their associated operative components may be controlled by a camming arrangement in which each control rod for each of the needle and fastener assemblies 62 has a cam follower, indicated for their respective control rods as 68f, 70f, 72f, 74f. Each cam follower is secured to the proximal end of its associated control rod. The cam followers for each needle and fastener assembly 62 are driven by a rotatable cam drum 76 having follower-receptive cam tracks 68t, 70t, 72t and 74t formed on a cylindrical sidewall 78 that defines the drum surface. The drum includes a front-end cap 79 attached to its distal end and a rear end cap 81 attached to it proximal end. A center shaft 83 is rotatably mounted to the frame 50 and the end caps are attached to the center shaft 83. The cam drum 76, end caps 79, 81 and center shaft 83 rotate as a unit. In the illustrative embodiment, the cam follower 74f for the needle control rod 74 engages cam track 74t, the cam follower 72f for the retention shaft control rod 72 engages the cam track 72t, the cam follower 70f for the proximal implant push tube control rod 70 engages cam track 70 t and the cam follower 68f for the retractable pin (or overtube) control rod 68 engages the cam track 68t.

Figure 16:
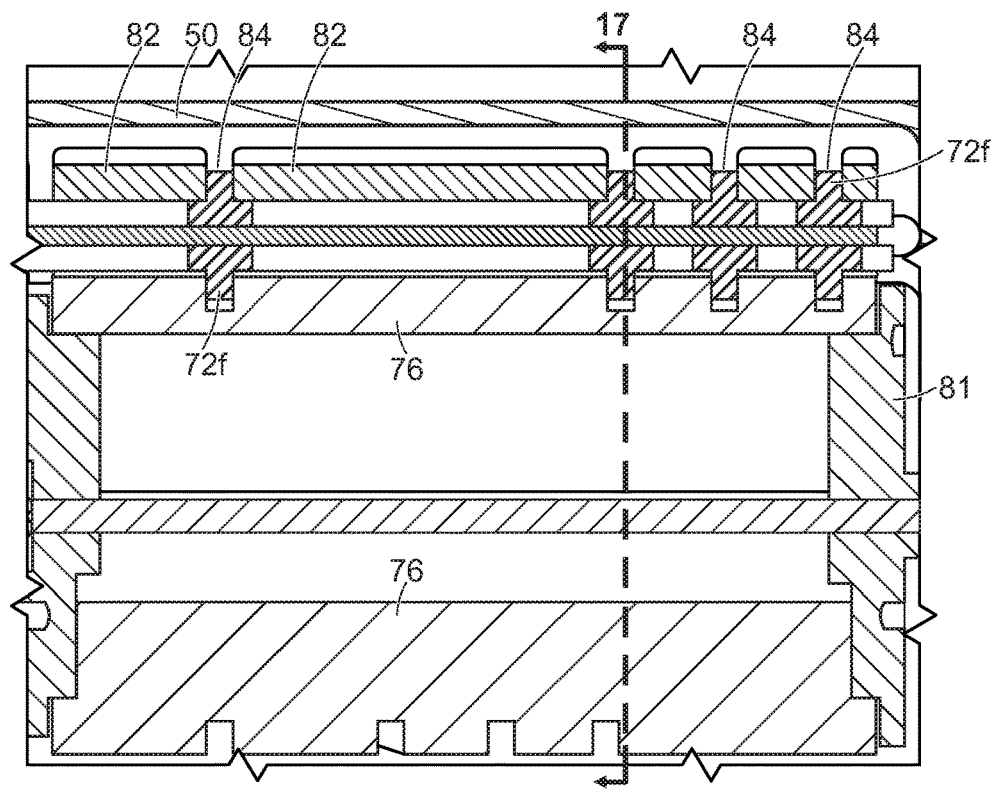
FIG. 16 is a sectional illustration of the spacer arrangement as seen along the plane 16-16 of FIG. 17.
Figure 17:
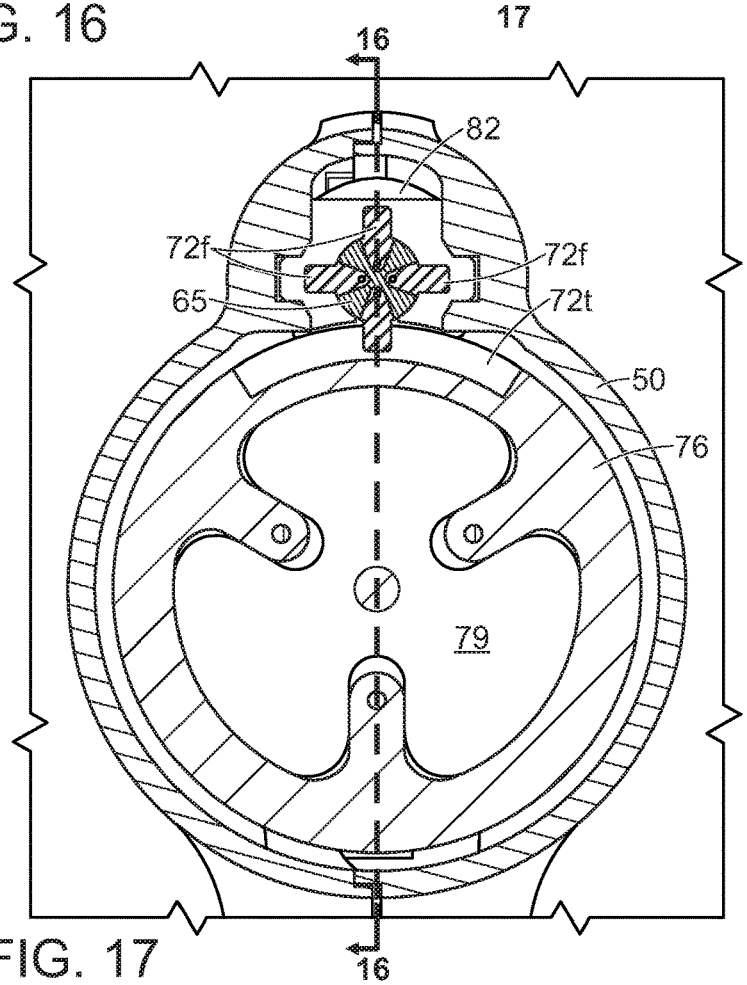
FIG. 17 is a sectional illustration of the spacer arrangement and cam followers as seen along the plane 17-17 of FIG. 16.

The device is arranged so that only the cam followers 68f, 70f, 72f and 74f of one group 66 of control rods are in engagement with the cam tracks 68t, 70t, 72t, 74t at a time. As shown in FIGS. 16 and 17 the cam followers for each group 66 of control rods extend radially outward from their supporting channels 63. The hub 56 and control rod support 65, mounted for rotation about the central axis 67, are associated with a detent mechanism 80 (FIG. 11) mounted to the front end of the housing that indexes the hub 56, control rod support 65 and associated control rod group 66 so that they are aligned with the active axis 64. When so aligned, only one group of cams followers is in engagement with the cam tracks of the cam drum 76. The cam followers of the other, inactive, control rods are maintained in a "starting position" (see FIGS. 11, 16 and 17) by a number of spacers 82 that are mounted to the housing 50, extend about the control rod support 65 and define gaps 84 receptive to the inactive cam followers. When one of the groups 66 of control rods is aligned along the active axis 64, the cam followers of the inactive groups extend about the central axis at what may be considered as the nine, twelve and three o'clock positions (viewed axially for a four-needle device; FIG. 17) to prevent axial movement of the inactive followers. The spacers, however, do not interfere with axial movement of the cam followers 68f, 70f, 72f and 74f in the six o'clock, active position so that the the cam followers of the active assembly 66 can protrude into and engage their associated cam tracks (FIG. 17). The gaps 84 between spacers maintain the inactive cam followers in their relative starting positions so that when a group 66 is rotated into an active position along the active axis 64, its cam followers will engage the cam tracks at their starting positions.

Figure 11:
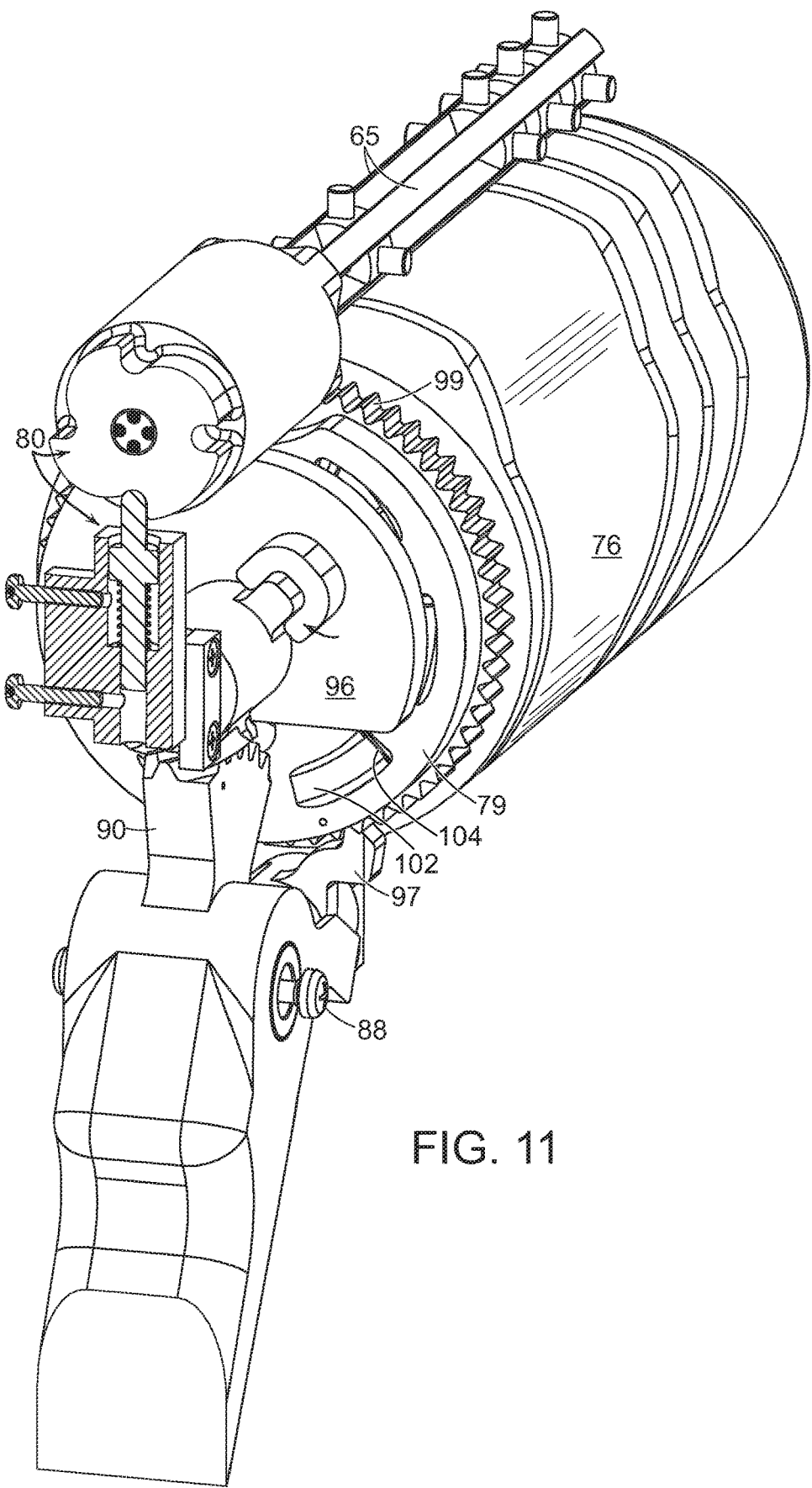
FIG. 11 is an isometric illustration of the front end of the drive mechanism of the deployment device.
Figure 14:
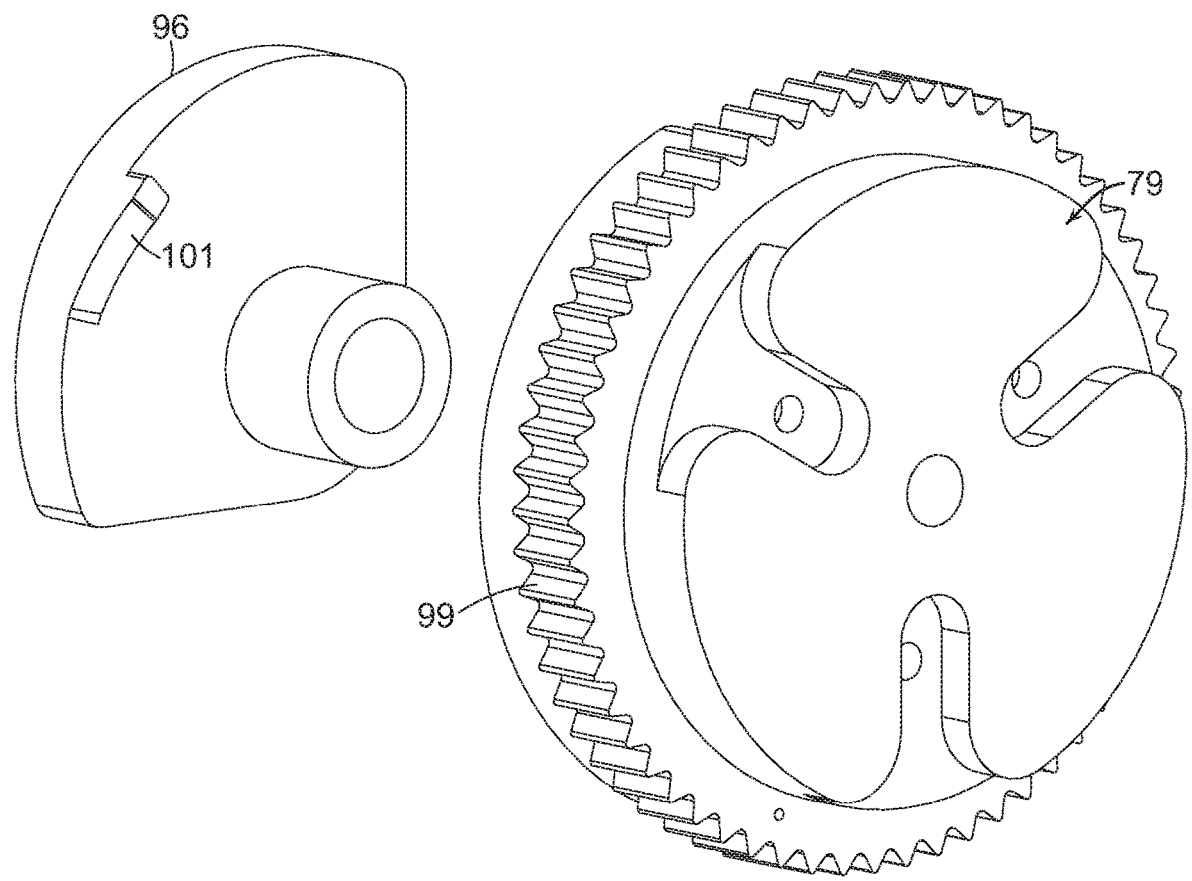
FIG. 14 is an exploded view of the rear face of the end cap and the clutch plate of the drive mechanism.
Figure 15:
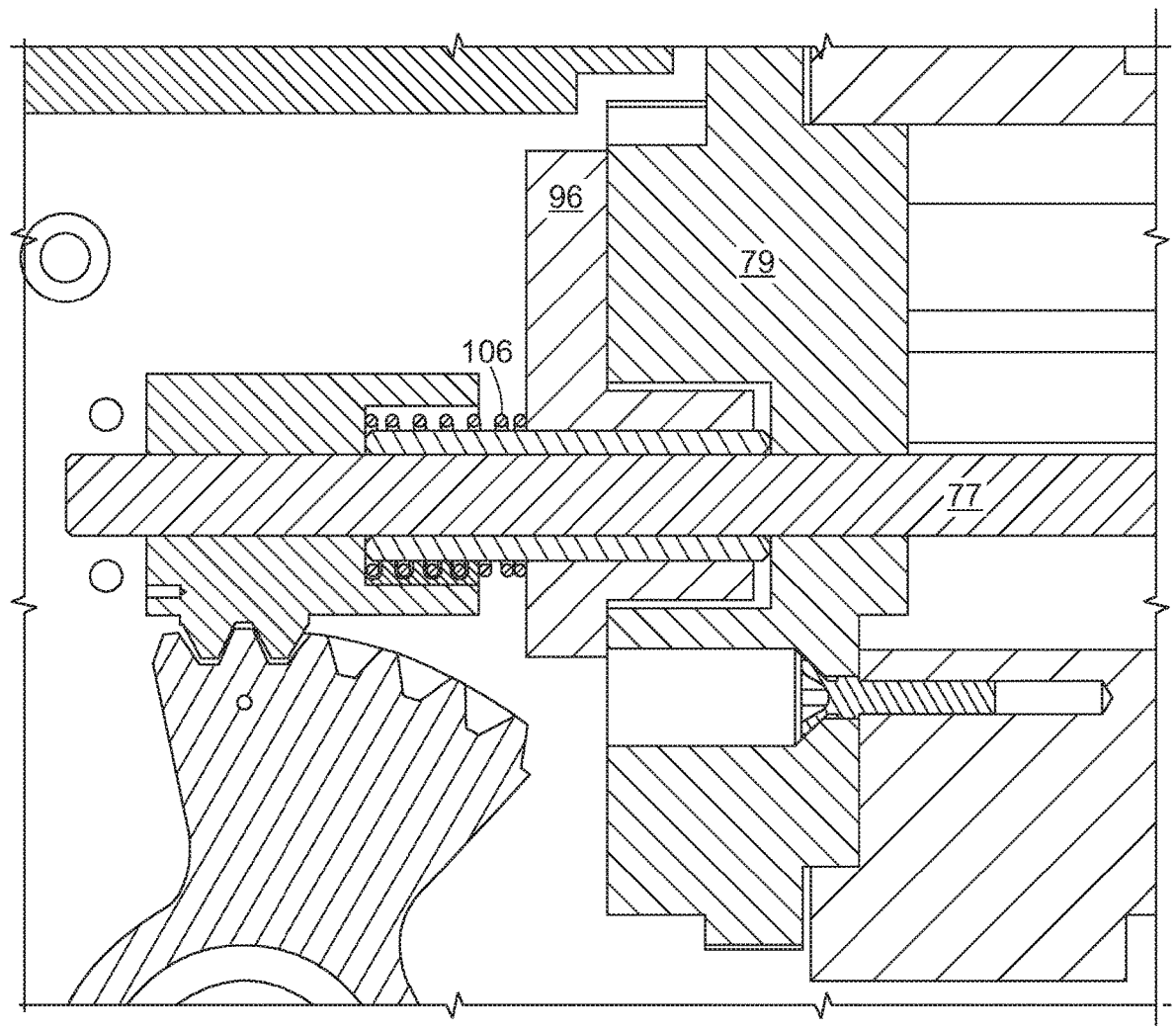
FIG. 15 is a sectional illustration of a portion of the drive mechanism.

The device is operated by a drive mechanism that rotates the cam drum 76 in a series of angular increments that drive the active cam followers and their respective control rods to perform the sequence of steps to deliver and deploy a fastener assembly. In the manually operated embodiment shown, the trigger 54 is pivoted to the housing 50 at pivot 88 and has a gear segment 90 that is in engagement with a skewed-axis gear segment 92 that is secured to or is formed integral with a drive member 94 (FIG. 13). The gear segments 90, 92 may have non-parallel, non-intersecting axes as in crossed helical gears. The drive member 94 is connected to a clutch plate 96 that, in turn, engages the front face 98 of front-end cap 79 to turn the cam drum. The front face of the front-end cap is provided with a number of circumferentially spaced, recessed, inclined ramps 102, each having a drive face 104 (FIG. 13). When the clutch plate 96 is rotated a, lug 101 (FIG. 14) on the surface of the clutch plate 96 that faces the front-end cap engages with the drive face 104 of ramp 102 to rotatably advance the drum (counter-clockwise as seen in FIGS. 11 and 13). With each squeeze of the trigger 54 the drive member 94 is rotated through a predetermined angular increment (sixty degrees in the illustrative embodiment) that is transmitted to the front-end cap 79 and the cam drum 76. The cam drum is prevented from rotating in a reverse direction by a spring-biased pawl 97 pivoted to the housing that engages teeth 99 formed along the periphery of the front-end cap 79. When the trigger is released it returns to its initial position by a trigger spring 100 causing the clutch plate 96 and drive member 94 to also return to their initial positions in readiness for the next advancement. In order to enable the clutch plate to return (clockwise as seen in FIG. 13) to a starting position, a return spring 106 (FIG. 15) biases the clutch plate 96 toward its starting position as well as biasing it into engagement with the front-end cap 79. The drive member 94 is connected to the clutch plate 96 by a lost-motion connection 97 that enables the clutch plate to move axially as its lug 101 slides up the inclined ramp 102.

FIG. 18 illustrates, in flat plane, the cam tracks that control operation of the device and FIGS. 16A-16J illustrate the sequential configurations of the distal end of the fastener deployment device and tissue that correspond to the sequential positions of the cam drum. When the cam drum and cam followers are in a starting position the active cam followers are at the beginning of the track as indicated at the top of the diagram and the active needle 40 is contained in its chamber in the wand. The first actuation of the trigger 54 rotates the drum to position 1 that moves the all of the cam followers 68f, 70f, 72f, 74f forwardly to expose the distal end of the needle beyond the distal end of the wand 58 while maintaining constant the relative positions of the other components with respect to the needle (FIG. 18B). At this point the operator passes the needle manually through the tissue layers to be fastened together so that the distal tip of the needle is located distally of the tissue layers (FIG. 18C). At the next actuation of the trigger 54 cam drum is rotated to position 2 in which the needle cam follower 74f remains extended while the proximal pusher cam follower 72f, the distal retention cam follower 70f and the pin cam follower 68f are advanced distally to push the distal implant 12 out of the distal end of the needle and self-expand to its deployed configuration FIG. 18D). The clinician may, at this point, retract the device slightly rearwardly to assure that the proximal implant 10, which is still in the needle 40, is positioned proximally of the tissue before it is deployed (FIG. 18E) In the next actuation of the trigger 54 to advance the cam drum to position 3 the cam tracks maintain the pusher, distal retention and pin cams stationary while retracting the needle thereby exposing the proximal implant on the proximal side of the tissue layers and enabling it to expand to its deployed configuration (FIG. 18F). The next actuation of the trigger advances the cam drum to position 4 to advance the pusher cam 70f distally while maintaining the position of the other cams to urge the proximal implant 10 towards the distal implant 10 until the latching mechanisms engage to secure the implants together (FIG. 18G. The next trigger actuation to cam drum position 5 partially retracts the pusher and the pin (FIG. 18H) to enable the mechanical interlock connection between the locking tube 26 and the retention shaft 31 to be separated by simple manipulation of the device (FIG. 18I). The final trigger actuation to position 6 retracts pusher, the distal retention and pin cam follower (FIG. 18J). With the cam followers returned to their starting positions, the hub 56 and associated components (control rod groups, control rod support, wand) can be rotated to rotate the next group of cam followers to the six o'clock position in engagement with the cam tracks as the previously active cam followers are rotated to inactive positions into the gaps 84 between the spacers 82.

From the foregoing it will be appreciated that the invention enables a clinician to apply a plurality of tissue fasteners to clamp tissue layers together and to occlude hollow or luminal anatomical structures and to do so in rapid succession.

It should be understood that although the illustrative embodiment describers a manually operated device, the invention may be practiced with a motorized device in which a battery-operated motor is used instead of the manual trigger mechanism. It also should be understood that the foregoing description of the invention is intended merely to be illustrative thereof and that other embodiments, modifications and equivalents may be apparent to those skilled in the art without departing from the principles of the invention.

The invention claimed is:

1. A delivery device for deploying multiple tissue fasteners comprising:
   a frame;
   a carrier for a plurality of needle and fastener assemblies, the carrier having multiple chambers, each containing a needle and fastener assembly that comprises:
      (i) a hollow needle adapted to be passed through tissue layers to be fastened,
      (ii) the needle containing, in tandem, a proximal implant and a distal implant, the implants being configured to self-expand when ejected from the needle, the implants being lockable to each other after ejection in response to drawing the implants together and
   control members operatively associated with the implants to eject the implants from the needle after the needle has been passed through tissue;
   the carrier being movably mounted on the frame to selectively align one of the carrier chambers with a delivery axis, the needle and fastener assembly aligned with the delivery axis comprising an active assembly, the other needle and fastener assemblies comprising inactive assemblies;
   each of the control members being movable along an axial direction; and
   a drive mechanism for operating the control members in a predetermined sequence and direction after the needle has been passed through tissue to eject the distal implant out of the needle distally of the tissue, then to eject the proximal implant from the needle proximally of the tissue, then to draw the proximal and distal implants toward each other to lock them together and then to release the delivery device from the implants.

2. A delivery device as defined in claim 1 wherein the drive mechanism comprises each of the control members having a cam follower;
   a plurality of movable camming surfaces, each engageable with an active needle and fastener assembly to control the axial position of each active cam follower of the active needle and fastener assembly and its associated control member; and
   means for incrementally moving the camming surfaces to move the cam followers and associated control members in the predetermined sequence.

3. The apparatus of claim 2 wherein the drive mechanism further comprises:
   a trigger associated with the camming surfaces to cause incremental advancement of the camming surfaces for each actuation of the trigger.

4. A delivery device as defined in claim 1 wherein the chambers are arranged in the carrier along parallel axes.

5. The delivery device of claim 1 further comprising:
   the carrier being rotatably mounted to the frame for rotation about a central axis;
   the delivery axis being offset and parallel to the central axis.

6. The delivery device of claim 5 further comprising:
   camming surfaces being formed on a cam drum, the drum being rotatably mounted to the frame for rotation about an axis parallel to the central and delivery axes.

7. The apparatus of claim 6 further comprising:
   a pawl associated with the cam drum for limiting the direction of rotation of the cam drum.

8. The delivery device of claim 5 wherein the carrier is manually rotatable.

9. The delivery device of claim 1 further comprising:
a needle control member associated with the needle with a cam follower at the proximal end of the needle control member;
the predetermined sequence and direction being preceded by advancement of the needle distally beyond the distal end of the carrier to enable the needle to be passed through tissue.

10. The delivery device of claim 1 further comprising:
a retainer mounted to the frame and engageable with the cam followers of the inactive needle and fastener assemblies to prevent axial movement of the inactive cam followers and to align and maintain the axial positions of the inactive cam followers in a starting position.

11. The delivery device of claim 10 wherein the retainer enables axial movement of the cam followers of the active needle and fastener assembly.

12. The apparatus of claim 10 wherein the retainer comprises:
a plurality of spacers aligned parallel to the delivery axis, the spacers defining gaps receptive to the cam followers, the gaps being sized and spaced to correspond to the starting positions of the cam followers;
each gap containing all of the cam followers;
cam followers of the active needle and fastener assembly extending toward and into engagement with their associated camming surfaces.

13. The delivery device of claim 1 in which there are at least four chambers, each containing a needle and fastener assembly.

14. The delivery device of claim 1 further comprising an indexing detent to secure the carrier to align a chamber in the active position.

15. The apparatus of claim 1 in which the drive mechanism
comprises a battery powered motor.

16. The apparatus of claim 1 wherein one of the control members comprises:
a distal implant retention shaft detachably connected at an interlock to the distal implant and having a control rod with a cam follower.

17. The apparatus of claim 1 wherein one of the control members comprises:
a proximal implant pusher shaft having a cam follower at its rearward end.

18. The apparatus of claim 1 wherein one of the control members comprises a removable locking rod extending through the interlock with a cam follower at its rear end.

19. The apparatus of claim 1 wherein one of the control members comprises an over tube extending over the interlock and having a cam follower at its rear end.

20. The apparatus as defined in claim 1 further comprising the implants being configured so that when brought together in the absence of tissue, the legs of the proximal implant are interdigitated with the legs of the distal implant.

21. A delivery device for deploying multiple tissue fasteners comprising:
a frame;
a carrier for a plurality of needle and fastener assemblies, the carrier having multiple chambers, each containing a needle and fastener assembly that comprises:
(i) a hollow needle adapted to be passed through tissue layers to be fastened, the needle containing a proximal implant and a distal implant, the implants being configured to self-expand when ejected from the needle, the implants being lockable to each other after ejection in response to drawing the implants together and
(ii) control members operatively associated with the implants to eject the implants from the needle after the needle has been passed through tissue;
the carrier being movable to selectively align one of the carrier chambers and its contained needle and fastener assembly with a delivery axis, the aligned needle and fastener assembly comprising an active assembly, the other needle and fasteners assemblies comprising inactive assemblies;
a drive mechanism operatively positioned with respect to the delivery axis and constructed to engage the control members of an active needle and fastener assembly to move the control members in a predetermined sequence and direction in which first, the needle is exposed distally of the carrier to enable the needle to be passed through tissue layers, then, after the needle has been passed through tissue to eject the distal implant out of the needle distally of the tissue, then to eject the proximal implant from the needle proximally of the tissue, then to draw the proximal and distal implants toward each other to lock them together and then to release the delivery device from the implants.

22. A delivery device as defined in claim 21 wherein the carrier is rotatable about a central axis and wherein the chambers are arranged in parallel to each other.

23. A method of delivering and deploying a plurality of tissue fasteners with a delivery device to fasten at least two tissue layers together comprising:
providing a carrier for a plurality of needle and fastener assemblies, the carrier having multiple chambers, each containing a needle and fastener assembly that comprises:
(i) a hollow needle adapted to be passed through tissue layers to be fastened, the needle containing a proximal implant and a distal implant, the implants being configured to self-expand when ejected from the needle, the implants being lockable to each other after ejection in response to drawing the implants together and
(ii) control members operatively associated with the implants to eject the implants from the needle after the needle has been passed through tissue;
positioning the carrier to selectively align one of the carrier chambers and its associated needle and fastener assembly with a delivery axis, the needle and fastener assembly aligned with the delivery axis comprising an active assembly, the other assemblies comprising inactive assemblies;
moving each of the control members in each active assembly axially in a direction and sequence in which, after the needle has been passed through tissue, first to eject the distal implant out of the needle distally of the tissue, then to eject the proximal implant from the needle proximally of the tissue, then to draw the proximal and distal implants toward each other to lock them together and then to release the delivery device from the implants;
repositioning the carrier to align another of the chambers with the delivery axis and repositioning the delivery device to another tissue location;
again, moving the control members of the repositioned carrier after the needle has been passed through tissue, first to eject the distal implant out of the needle distally of the tissue, then to eject the proximal implant from the needle proximally of the tissue, then to draw the proximal and distal implants toward each other to lock them together and then to release the delivery device from the implants.

\* \* \* \* \*